(12) United States Patent
Dwivedi et al.

(10) Patent No.: US 8,115,015 B2
(45) Date of Patent: Feb. 14, 2012

(54) PROCESS FOR THE PREPARATION OF AMORPHOUS ATORVASTATIN CALCIUM

(75) Inventors: Shriprakash Dhar Dwivedi, Ahmedabad (IN); Dhimant Jasubhai Patel, Ahmedabad (IN); Kishor Maneklal Vinchhi, Ahmedabad (IN); Mahesh Laljibhai Rupapara, Ahmedabad (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 192 days.

(21) Appl. No.: 12/359,467

(22) Filed: Jan. 26, 2009

(65) Prior Publication Data
US 2010/0190999 A1    Jul. 29, 2010

(51) Int. Cl.
*C07D 207/00* (2006.01)
(52) U.S. Cl. ........................................................ 548/537
(58) Field of Classification Search .................... 548/537
See application file for complete search history.

(56) References Cited

U.S. PATENT DOCUMENTS

| | | |
|---|---|---|
| 4,681,893 A | 7/1987 | Roth |
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth |
| 5,342,952 A | 8/1994 | Butler et al. |
| 5,397,792 A | 3/1995 | Butler et al. |
| 5,969,156 A | 10/1999 | Briggs et al. |
| 6,087,511 A | 7/2000 | Lin et al. |
| 6,121,461 A | 9/2000 | McKenzie |
| 6,750,353 B2 | 6/2004 | Sorsak |
| 7,208,608 B2 | 4/2007 | Radl et al. |

FOREIGN PATENT DOCUMENTS

| | | |
|---|---|---|
| EP | 1659110 | 5/2006 |
| WO | WO0071116 | 11/2000 |

OTHER PUBLICATIONS

Konno, T., Chem. Pharm. Bull., 1990, vol. 38, pp. 2003-2007.
Wall, G. M., Pharm Manuf., 1986, vol. 3, pp. 33.
Haleblian, J.K. and McCrone, W., J. Pharm. Sci., 1969, vol. 58, pp. 911.
Haleblian, J.K., J. Pharm. Sci., 1975, vol. 64, pp. 1269.

*Primary Examiner* — Rebecca Anderson
*Assistant Examiner* — Samantha Shterengarts
(74) *Attorney, Agent, or Firm* — IpHorgan Ltd.

(57) ABSTRACT

The present invention also provides the amorphous form of hemi-calcium salt of atorvastatin with high purity and processes for preparation thereof.

9 Claims, 1 Drawing Sheet

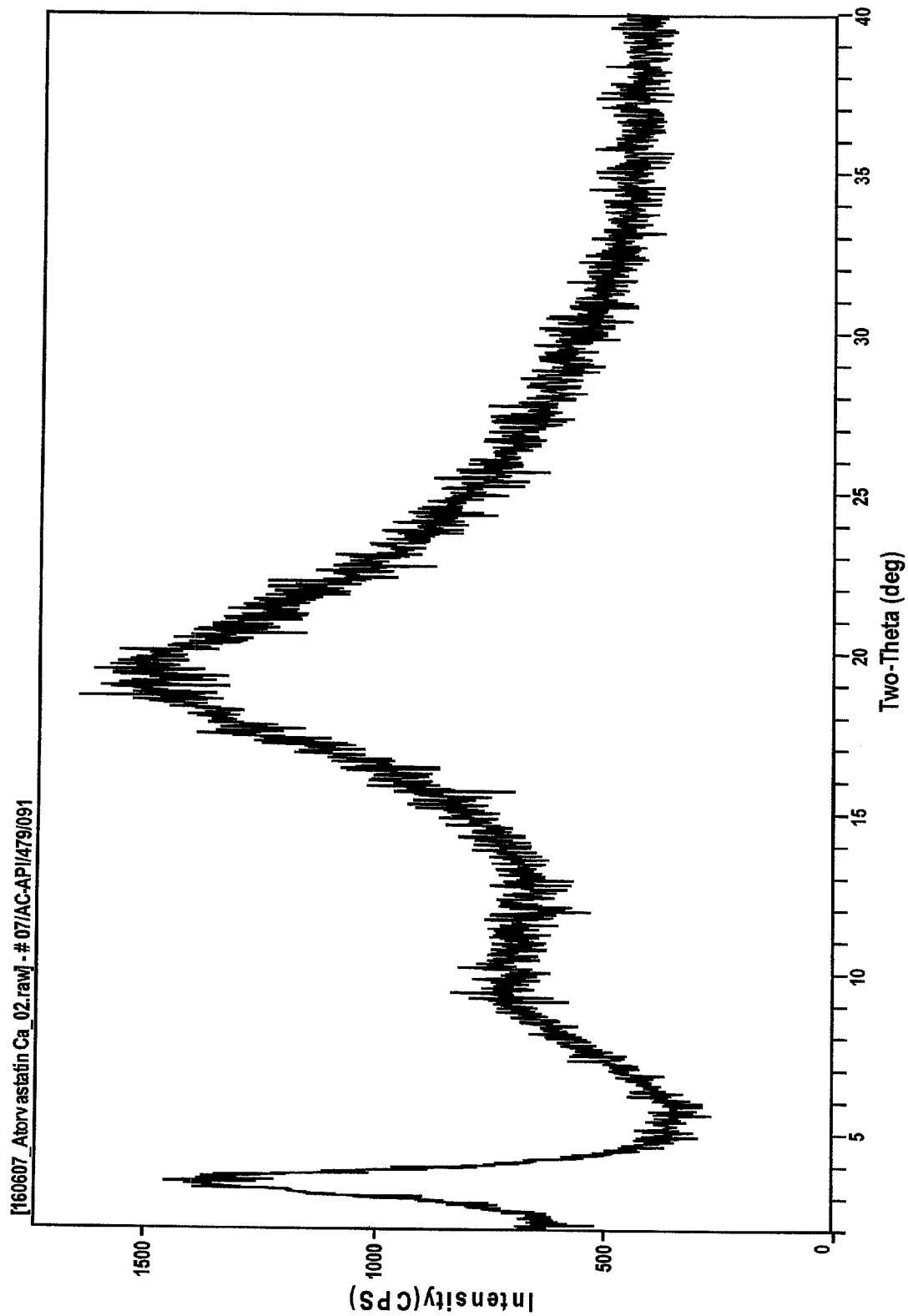

PROCESS FOR THE PREPARATION OF AMORPHOUS ATORVASTATIN CALCIUM

BACKGROUND OF THE INVENTION

1. Field of the Invention

The invention relates to improved process for preparation of an amorphous form of the hemi-calcium salt of atorvastatin in stable form. The present invention also provides the amorphous form of hemi-calcium salt of atorvastatin with high purity. Atorvastatin calcium is known as hemi-calcium salt of (3R, 5R) 7-[3-phenyl-4-phenylcarbamoyl-2-(4-fluorophenyl)-5-isopropyl-pyrrol-1-yl]-3,5-dihydroxyheptanoic acid of formula (I).

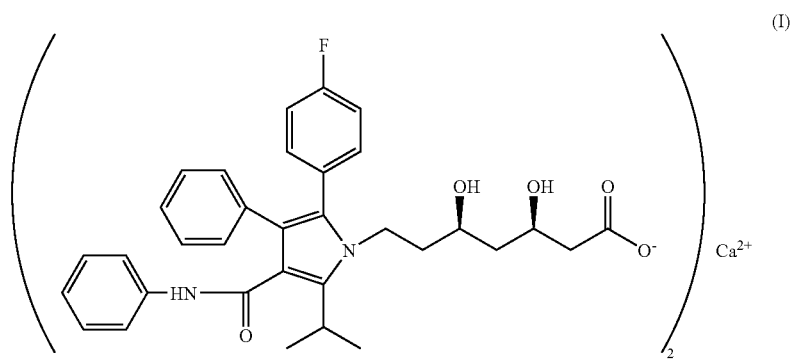

Any discussion of the prior art throughout the specification should in no way be considered as an admission that such prior art is widely known or forms part of common general knowledge in the field.

Atorvastatin (formula I) is manufactured according to published patents (U.S. Pat. Nos. 4,681,893; 5,003,080; 5,097,045; 5,103,024; 5,124,482; 5,149,837; 5,155,251; 5,216,174; 5,245,047; 5,248,793; 5,273,995; 5,397,792; 5,342,952) and its calcium salt is usually made from sodium salt of (3R,5R)-7-[3-phenyl-4-phenylcarbamoyl-2-(4-fluorophenyl)-5-isopropyl-pyrrol-1-yl]-3,5-dihydroxyheptanoic acid and a suitable, water soluble calcium salt, preferably from calcium acetate or chloride. Atorvastatin is usually prepared as the calcium salt since this enables atorvastatin to be conveniently formulated in pharmaceutical formulations, for example, in tablets, capsules, powders and the like for oral administration.

The starting sodium salt of (3R,5R)-7-[3-phenyl-4-phenylcarbamoyl-2-(4-fluorophenyl)-5-isopropyl-pyrrol-1-yl]-3,5-dihydroxyheptanoic acid may be obtained from the said acid, which is normally obtained from (3R,5R) tert-butyl (6-{2-[3-phenyl-4-phenylcarbamoyl-2-(4-fluorophenyl)-5-isopropyl-pyrrol-1-yl]-ethyl}-2,2-dimethyl-[1,3]dioxane-4-yl)-acetate (formula II).

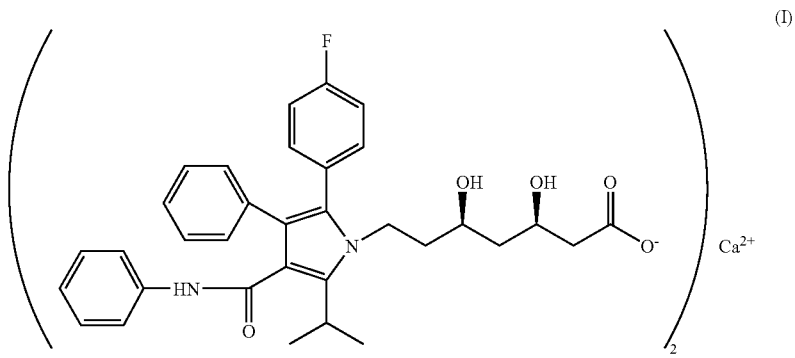

(I)

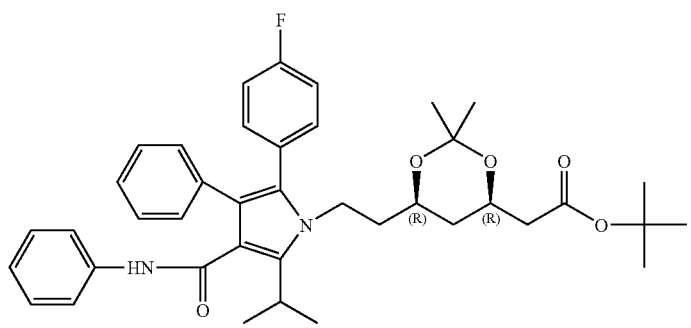

(II)

This key intermediate is converted to the sodium salt of the respective acid first by mixing with hydrochloric acid and, later on, with a large excess of sodium hydroxide, which is, however, accompanied with a large amount of excess hydroxide and also of sodium chloride. Acidification followed by extraction then affords a solution of the respective acid (formula III) without any inorganic impurities. Thus obtained acid is then converted to the respective lactone (formula IV), which can be purified by crystallization, and the purified lactone is then converted to the sodium salt by mixing with an equivalent of sodium hydroxide; an excess cannot be used as it would form, with the calcium salt, calcium hydroxide in the next step that could not be fully removed from the product in the follow up process steps according to the above patents. However, when an equivalent of the hydroxide is used the reaction is time consuming and it has to be monitored by HPLC. Another disadvantage of this process is loss of approximately 20% of the yield.

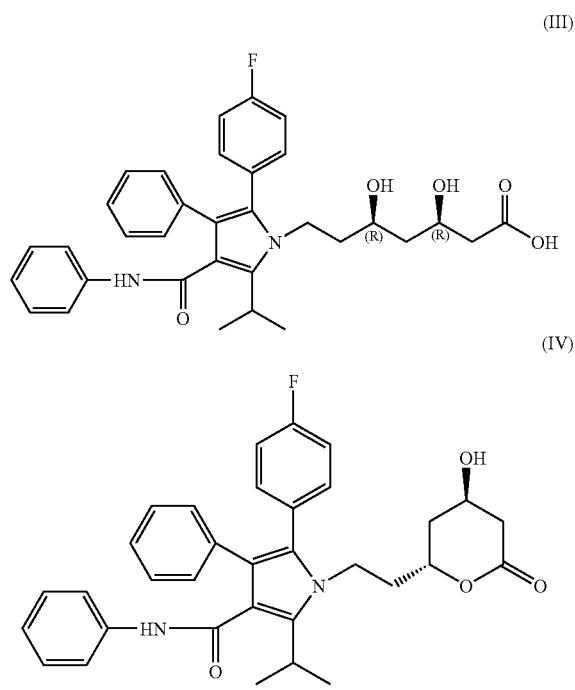

(III)

(IV)

Atorvastatin calcium can exist in amorphous form or in various known crystalline forms like Form I, Form II, Form III and Form IV, which are disclosed in International Publications Nos. WO 97/3958 (U.S. Pat. No. 6,121,461) and WO 97/3959 (U.S. Pat. No. 5,969,156). It is known that the amorphous forms of a number of pharmaceutical substances exhibit different dissolution characteristics and bioavailability patterns compared to the crystalline forms (Konno T., Chem. Pharm. Bull., 1990, 38:2003-2007). For some therapeutic indications the bioavailability is one of the key parameters determining the form of the substance to be used in a pharmaceutical formulation. Since processes for the crystallization and the preparation, respectively, of the amorphous substance are sometimes difficult, and sometimes afford amorphous-crystalline mixtures, that is, a crystalline form instead of an amorphous form, there is a constant need for processes which enable the preparation of a non-crystalline form without simultaneous formulation of crystalline forms, that is, which will enable the conversion of the crystalline form into the non-crystalline form.

Atorvastatin calcium is a substance, which is very slightly water-soluble, and it has been found that the crystalline forms are less readily soluble than the amorphous form, which may cause problems in the bioavailability of atorvastatin in the body. It has been found that the production of amorphous atorvastatin calcium according to the previously disclosed processes was not consistently reproducible, and therefore a process has been developed for converting the crystalline forms of atorvastatin calcium (formed in the synthesis of atorvastatin) to the amorphous form. The process is described in International Publication No. WO 97/3960 (U.S. Pat. No. 6,087,511) and comprises dissolving a crystalline form of atorvastatin calcium in a non-hydroxylic solvent and removing the solvent to afford amorphous atorvastatin calcium. The preferred non-hydroxylic solvent is selected from the group consisting of tetrahydrofuran and a mixture of tetrahydrofuran and toluene. The disadvantage of the above process is primarily use of non-nature-friendly solvents.

A similar process is described in International Publication No. WO 00/71116 and comprises dissolving the crystalline form of atorvastatin calcium in a non-hydroxylic solvent, such as, for example, tetrahydrofuran. To the solution of atorvastatin calcium is added a non-polar organic solvent, or the solution of atorvastatin calcium is added to a non-polar organic solvent, to allow atorvastatin calcium to precipitate. The formed precipitate is filtered off.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, *Pharm Manuf.* 3, 33 (1986); J. K. Haleblian and W. McCrone, *J. Pharm. Sci.*, 58, 911 (1969); and J. K. Haleblian, *J. Pharm. Sci.*, 64, 1269 (1975), all of which are incorporated herein by reference.

U.S. Pat. No. 7,208,608 B2 discloses a method of manufacturing an amorphous form of the hemi-calcium salt of (3R,5R) 7-[3-phenyl-4-phenylcarbamoyl-2-(4-fluorophenyl)-5-isopropyl-pyr-rol-1-yl]-3,5-dihydroxyheptanoic acid, in which (3R,5R)-7-[3-phenyl-4-phenylcarbamoyl-2-(4-fluorophenyl)-5-isopropyl-pyrrol-1-yl]-3,5-dihydroxy heptanoic acid or its salt with a cation $M^+$ wherein $M^+$ is either a cation of an alkali metal or an ammonium cation of formula $R_nN^{(+)}H_{(4-n)}$ wherein R is lower $C_1$-$C_5$ alkyl, n may reach values ranging between 0 and 3, is, without isolating the intermediate in the form of the hemi-calcium salt or of another salt, acid or lactone, converted, in a solution, by the treatment with the calcium salt or calcium hydroxide, or a calcium $C_1$-$C_5$ alcoholate, to the hemi-calcium salt, and the latter is precipitated with a $C_1$-$C_5$ hydrocarbon or dialkylether of formula $R_1OR_2$, wherein each of $R_1$ and $R_2$ is a $C_1$-$C_5$ alkyl group. The starting acid or its salt is prepared starting from (3R,5R) tert-butyl (6-{2-[3-phenyl-4-phenylcarbamoyl-2-(4-fluorophenyl)-5-isopropyl-pyrrol-1-yl]-ethyl}-2,2-dimethyl-[1,3]dioxane-4-yl)acetate.

U.S. Pat. No. 6,750,353 B2 provides the process for preparation of pharmaceutically acceptable atorvastatin salts in non-crystalline form, which comprises of providing a solution in a non-hydroxylic solvent like tetrahydrofuran of compound of formula II, shown below:

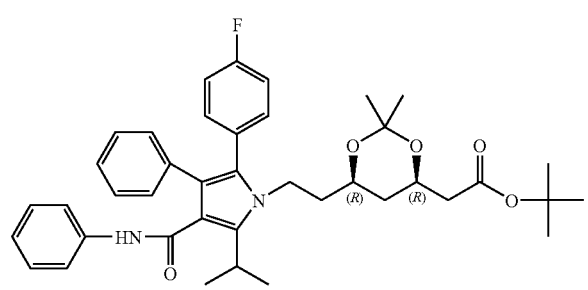

II followed by deprotection of the hydroxy and acid protecting group and adding a solvent which is slightly miscible or immiscible with water and in which the pharmaceutically acceptable salt is insoluble or practically insoluble like hexane, heptane, cyclohexane, ether and diisopropyl ether, etc., further followed by neutralizing the aqueous phase and converting atorvastatin into pharmaceutically acceptable salt.

EP 1,659,110 A1 claims the process for production of amorphous atorvastatin calcium and stabilized, amorphous atorvastatin calcium. The process provided for production of stabilized amorphous atorvastatin calcium comprises of dissolving crystalline atorvastatin calcium and an antioxidant in a solvent and adding the solution to an antisolvent, and obtaining stabilized amorphous atorvastatin calcium. The stabilized amorphous form of atorvastatin calcium is claimed containing not more than 0.2% of various impurities by HPLC and 0.5% of total impurities. Also, the relative stability after 3 months at 25° C./60% RH is provided.

U.S. Pat. No. 7,208,608 B2 of M/s Zentiva provides the process for preparation of atorvastatin calcium in amorphous form. However, the patent clearly discloses the extraction of sodium salt with ethyl acetate or crystallization of sodium salt of atorvastatin in ethanol followed by treatment with ethyl acetate, which may results in higher atorvastatin lactone content.

Further, atorvastatin calcium obtained as per process in U.S. Pat. No. '608 B2 suffers the disadvantage that the product required prolonged drying conditions to remove residual ethyl acetate or hydrocarbon solvents. The product does not meet the residual solvent requirements as per ICH limits. Hydrocarbons like cyclohexane, hexane etc. are class 2 solvents having limits of 3880 ppm and 290 ppm, respectively. It is extremely difficult to obtain residual solvents below these limits by the process as per U.S. Pat. No. '608 B2.

Thus, there is still a need to provide a very cost effective and industrially viable process for large-scale productions for the preparation of stabilized amorphous atorvastatin calcium.

SUMMARY OF THE INVENTION

It is one object of the present invention to provide a process for preparation of stable amorphous form of atorvastatin calcium.

It is also an object of the present invention to provide stabilized amorphous atorvastatin calcium in high purity without involving any excessive purification or purification by salt formation like ammonium salt, etc.

A further object of the present invention is to provide amorphous atorvastatin calcium in high purity having single individual unknown impurity less than 0.1% and single individual known impurity less than 0.15% with total impurities not more than 0.5% by HPLC.

Still another object of the present invention is to overcome the problems associated with the prior art process and to prepare atorvastatin by simple, cost effective, non-hazardous and easily scaleable way.

As used here in term "tert-butyl ester" means it represents [R—(R*,R*)]-1,1-dimethylethyl-2-(4-fluorophenyl)-dihydroxy-5-(1-methylethyl)-3-phenyl-4-[(phenylamino)carbonyl]-1H-pyrrole-1-heptanoate.

An improved process for preparation of an amorphous form of atorvastatin calcium of formula I

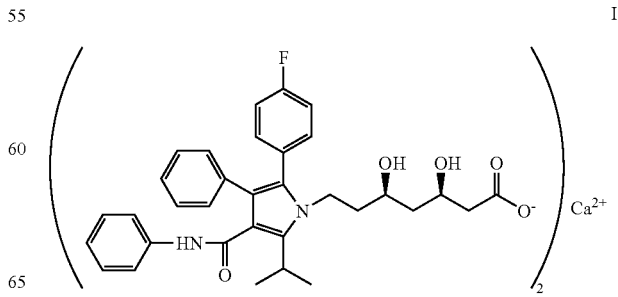

I which comprises alkaline hydrolysis of a tert-butyl ester of formula (IIa) in a suitable organic solvent;

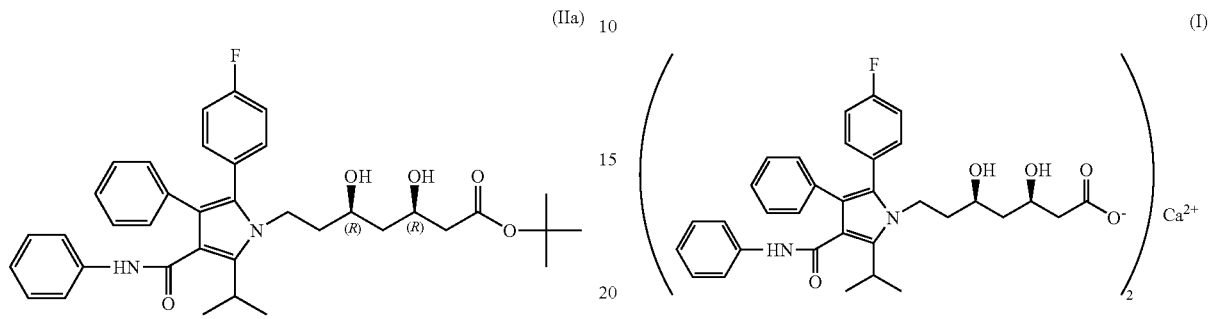

concentrating the reaction mixture to obtain residue;

adding water, ethyl acetate and ammonia to residue;

addition of molar excess of calcium acetate;

separating ethyl acetate layer, optionally washing ethyl acetate layer with ammonical water;

distilling ethyl acetate and treating with $C_5$-$C_{12}$ hydrocarbon solvent;

optionally slurring amorphous atorvastatin calcium with $C_1$-$C_5$ dialkyl ethers to obtain amorphous atorvastatin calcium.

The present invention provides an improved method of manufacturing an amorphous form of Atorvastatin calcium without isolating the intermediary any other crystalline hemi-calcium salt or of another salt, acid or lactone.

It has been surprisingly found that use of excess mole of calcium acetate and treatment of ammonia in the process provides substantially pure amorphous form of atorvastatin calcium, which is also stable and can be use in pharmaceutical composition.

Thus, according to one of the aspect there is provided a substantially amorphous form of atorvastatin calcium by the present process of invention.

BRIEF DESCRIPTION OF THE DRAWINGS

The present invention will now be discussed in further detail below with reference to the accompanying FIGURE in which:

FIG. 1 is a graph illustrating the purity of the Atorvastatin calcium derived by the inventive process.

DETAILED DESCRIPTION OF THE PREFERRED EMBODIMENTS

According to the present invention, there is provided an improved process for preparation of an amorphous form of atorvastatin calcium of formula I

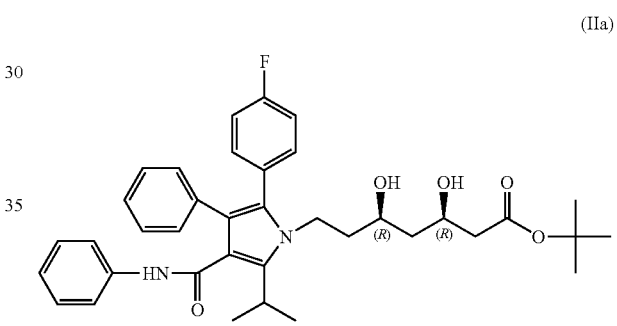

which comprises:

alkaline hydrolysis of a tert-butyl ester of formula (IIa) in a suitable organic solvent;

(IIa)

concentrating the reaction mixture to obtain residue; adding water, ethyl acetate and ammonia to residue;

addition of molar excess of calcium acetate; separating ethyl acetate layer, optionally washing ethyl acetate layer with ammonical water;

distilling ethyl acetate and treating with $C_5$-$C_{12}$ hydrocarbon solvent; and optionally slurring amorphous atorvastatin calcium with $C_1$-$C_5$ dialkyl ethers to obtain amorphous atorvastatin calcium.

The present invention provides an improved method of manufacturing an amorphous form of Atorvastatin calcium without isolating the intermediary or any other crystalline hemi-calcium salt or of another salt, acid or lactone.

It has been surprisingly found that use of excess mole of calcium acetate and treatment of ammonia in the process provides substantially pure amorphous form of atorvastatin calcium, which is also stable and can be use in pharmaceutical composition.

The present invention also provides an improved process for preparation of an amorphous form of atorvastatin calcium of formula I

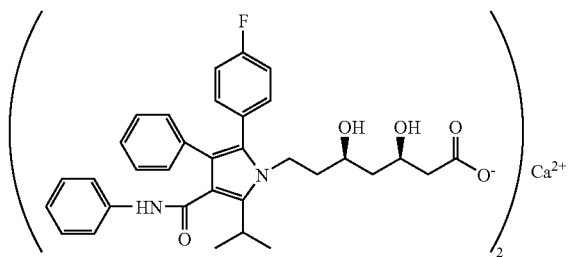

which comprises:

treating (3R,5R) tert-butyl (6-{2-[3-phenyl-4-phenylcarbamoyl-2-(4-fluorophenyl)-5-isopropyl-pyrrol-1-yl]-ethyl}-2,2-dimethyl-[1,3]dioxane-4-yl)acetate of formula (II) suitable acid to obtain tert-butyl ester of formula Ia and insitu alkaline hydrolysis of a tert-butyl ester of formula (IIa) in a suitable organic solvent;

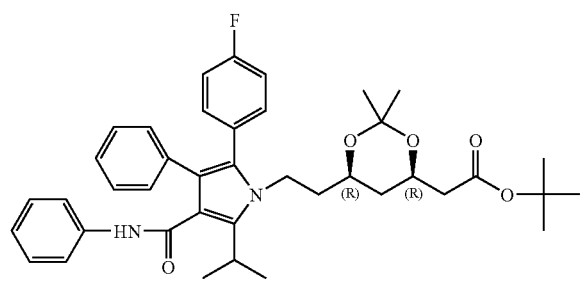

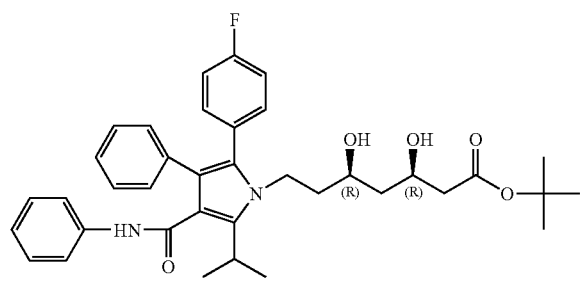

concentrating the reaction mixture to obtain residue;
adding water, ethyl acetate and ammonia to residue;
addition of molar excess of calcium acetate;
separating ethyl acetate layer;
optionally washing ethyl acetate layer with ammonical water;
distilling ethyl acetate and treating with $C_5$-$C_{12}$ hydrocarbon solvent; and
optionally slurring amorphous atorvastatin calcium with $C_1$-$C_5$ dialkyl ethers to obtain amorphous atorvastatin calcium.

In a preferred aspect of the present invention, (3R,5R) tert-butyl (6-{2-[3-phenyl-4-phenylcarbamoyl-2-(4-fluorophenyl)-5-isopropyl-pyrrol-1-yl]-ethyl}-2,2-dimethyl-[1,3]dioxane-4-yl)acetate of formula (II) is treated with suitable acid preferably hydrochloric acid in suitable organic solvent to provide tert-butyl ester of formula (IIa), which is further in situ treated with alkaline salt such as sodium hydroxide, potassium hydroxide, sodium carbonate in a suitable organic solvent, which results in alkaline salt of Atorvastatin; Preferably, alkaline hydrolysis of tert-butyl ester of formula (IIa) is performed with sodium hydroxide in suitable organic solvent such as methanol, ethanol, isopropanol, tetrahydrofuran, acetonitrile. The preferred solvent is acetonitrile.

The alkaline hydrolysis of tert-butyl ester of formula (IIa) is also reported in the prior art and can be used in the present invention.

According to preferred embodiment, upon alkaline hydrolysis of tert-butyl ester of formula (IIa); the organic solvent is removed and reaction mass is concentrated to obtain residue either in the form of solid or slurry then water is added to the said residue followed by addition of ethyl acetate solvent and liquor ammonia.

In alternative embodiment, water and liquor ammonia can be premixed and added as ammonical solution in the reaction mass and means to include with in the scope of the claims.

The reaction mass is stirred and molar excess of calcium acetate solution in water is added to the reaction mass. The calcium acetate can be use of about 1.1 to about 2.5 molar equivalent, preferably about 1.2 to about 1.8, more preferably about 1.5 molar equivalent so that pH of reaction mass is alkaline preferably, about 7 to 8.

The ethyl acetate layer containing atorvastatin calcium is separated by extraction. The ethyl acetate layer further treated with ammonia or amino acid like L-Lycine or L-Arginine. In the preferred, embodiment, the ethyl acetate layer is treated with ammonia, most preferably, ethyl acetate layer is washed with ammonical water.

Optionally, the ethyl acetate layer was treated with suitable anti-oxidant selected from the group consisting of butylated hydroxyanisole, butylated hydroxytoluene, tertiary-butylated hydroxyquinone, 4-methoxy anisole and the like, preferably butylated hydroxytoluene.

The ethyl acetate layer is concentrated by distillation and treated with $C_5$-$C_{12}$ hydrocarbon solvent selected from pentane, hexane, heptane, cyclohexane or mixtures thereof to provide amorphous form of atorvastatin calcium.

Optionally, thus obtained amorphous form of atrovastatin calcium is slurried with $C_1$-$C_5$ dialkyl ethers to obtain amorphous atorvastatin calcium, which is substantially pure and stable.

According to the preferred embodiments, (3R,5R) tert-butyl (6-{2-[3-phenyl-4-phenylcarbamoyl-2-(4-fluorophenyl)-5-isopropyl-pyrrol-1-yl]-ethyl}-2,2-dimethyl-[1,3]dioxane-4-yl)acetate of formula (II) is treated with hydrochloric acid is suitable organic solvent like methanol, ethanol, thetrahydrofuran, acetonitrile, acetone, ethyl acetate, 1,4-dioxane at about room temperature and stirred. Upon formation of tert-butyl ester of formula (IIa), alkaline salt solution, preferably sodium hydroxide solution was added to the reaction mass for alkaline hydrolysis. The pH of the reaction mass was adjusted to about 7.5 to 9, preferably 8.0 to 8.5 by addition of hydrochloric acid and extracted with organic solvent to remove impurities. The preferred organic solvent for extraction can be selected from ethereal solvent like di isopropyl ether, di ethyl ether, methyl tert-butyl ether.

The organic layer was removed and reaction mass concentrated to provide residue. Further, water, ethyl acetate and liquor ammonia were added to residue. In alternative embodiment, water and liquor ammonia can be premixed and added as ammonical solution in the reaction mass and means to include with in the scope of the claims. The amount of water added to the concentrated mass is equal to that of an ethyl acetate followed by slow addition of ethyl acetate to obtain clear solution followed by treatment with excess of calcium acetate whereby adjusting the pH to just alkaline i.e. about 8.0. The reaction mixture is maintained for 2 hours at 35° C. to 40° C. followed by cooling to 30° C. to 35° C.

The ethyl acetate layer containing atorvastatin calcium is separated by extraction. The ethyl acetate layer further treated with ammonia solution or amino acid like L-Lycine or L-Arginine. In the preferred, embodiment, the ethyl acetate layer is treated with ammonia, most preferably, ethyl acetate layer is washed with ammonical water.

Optionally, the ethyl acetate layer was treated with suitable anti-oxidant selected from the group consisting of butylated hydroxyanisole, butylated hydroxytoluene, tertiary-butylated hydroxyquinone, 4-methoxy anisole and the like, preferably butylated hydroxytoluene.

The ethyl acetate layer is concentrated by distillation and treated with $C_5$-$C_{12}$ hydrocarbon solvent selected from pentane, hexane, heptane, cyclohexane or mixtures thereof to provide amorphous form of atorvastatin calcium.

The partially wet cake was treated with ethereal solvents like diisopropyl ether, diethyl ether, methyl tert-butyl ether etc, preferably diethyl ether to obtain slurry. The slurry was filtered and dried obtain stabilized amorphous form of hemi-calcium salt of atorvastatin having X-ray powder diffraction pattern substantially as depicted in FIG. 1.

The stable amorphous atorvastatin calcium contains about 1000 to about 1500 ppm of antioxidants like herein above.

Stability is major concern for amorphous atorvastatin calcium. Atorvastatin lactone impurity increases during hydrolysis of sodium or calcium salt or even during stability. Hence, it is necessary to have atorvastatin lactone less than about 0.1% initially. This is achieved by providing the alkaline conditions to product during reaction as well as during stablility. The process of the present invention provides the solution for stabilizing atorvastatin calcium by treating ethyl acetate solution containing atorvastatin calcium with liq ammonia.

During alkaline hydrolysis of compound of formula Ia with sodium hydroxide, there are also chances of formation of atorvastatin lactone, which is avoided in the process of present invention by treatment with liq. ammonia to provide more alkaline conditions.

The inventors of the present invention has found that slurring the wet-cake of amorphous atorvastatin calcium containing ethyl acetate and hydrocarbons like cyclohexane and hexane in $C_1$-$C_5$ dialkyl ether solvents to obtain amorphous atorvastatin calcium substantially free from residual solvents well within ICH limits.

The present invention provides stable amorphous form of atorvastatin calcium by the process described herein above having either of characteristics:

The stable amorphous atrovastatin calcium having single individual unknown impurities less than about 0.1% and single individual known impurities less than 0.15%. area percentage of HPLC, when measured at 25°±2° C./RH 60±5% for 6 months.

The stable amorphous atrovastatin calcium having single individual unknown impurities less than of about 0.1% and single individual known impurities less than 0.15% by area percentage of HPLC, when measured at 20 to 8° C. under cold (5° C.) condition for 6 months.

The stable amorphous atrovastatin calcium having single individual impurities like atorvastatin diasteroisomer is less than 0.1%, atorvastatin desfluoro calcium is less than 0.1%, atorvastatin lactone is less than 0.1%, atorvastatin diol methyl ester is less than 0.1%, 3-O-methyl atorvastatin is less than 0.1%, t-butyl diol ester is less than 0.1% and atorvastatin protected diol is less than 0.1% by area percentage of HPLC, when measured at 25°±2° C./RH 60±5% for 6 months.

The stable amorphous atrovastatin calcium having single individual impurities like atorvastatin Diasteroisomer is less than 0.1%, atorvastatin desfluoro calcium is less than 0.1%, atorvastatin lactone is less than 0.1%, atorvastatin diol methyl ester is less than 0.1%, 3-O-methyl atorvastatin is less than 0.1%, t-butyl diol ester is less than 0.1% and atorvastatin protected diol is less than 0.1% by area percentage of HPLC, when measured at 2° to 8° C. under cold (5° C.) condition for 6 months.

The amorphous form of atorvastatin calcium as obtained by process as described herein above and characterized by x-ray powder diffraction pattern as substantially as depicted in FIG. 1 in substantially pure amorphous form having single individual unknown impurities less than 0.1% and single individual known impurities less than 0.15% and total impurities less than 0.45% by HPLC.

Although the invention has been described with reference to a specific example, it will be appreciated by those skilled in the art that the invention may be embodied in many other forms.

The process of the present invention will be explained in more detail with reference to the following examples, which are provided by way of illustration only and should not be constructed as limit to the scope of the claims in any manner.

Example-1

Preparation of [R—(R*,R*)]-1,1-dimethylethyl-2-(4-fluorophenyl)-dihydroxy-5-(1-methylethyl)-3-phenyl-4-[(phenylamino)carbonyl]-1H-pyrrole-1-heptanoate

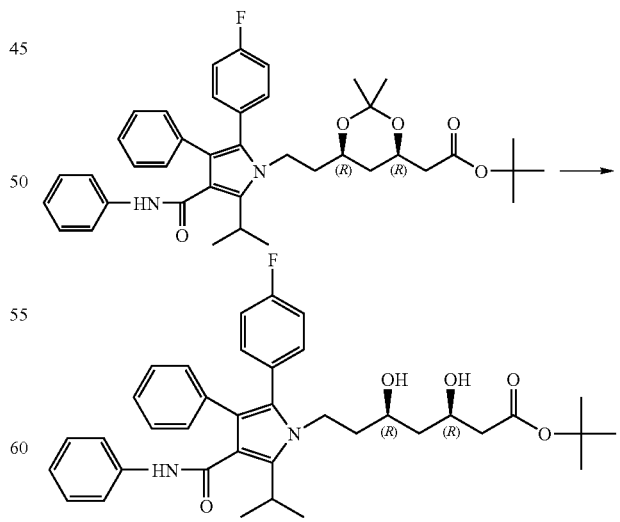

100 gm of (3R,5R) tert-butyl (6-{2-[3-phenyl-4-phenylcarbamoyl-2-(4-fluorophenyl)-5-isopropyl-pyrrol-1-yl]-ethyl}-2,2-dimethyl-[1,3]dioxane-4-yl)acetate and 1 Lit acetonitrile were taken in round bottom flask. 100 mL 1N HCl solution in 300 mL of water was added dropwise at 30° C. to 35° C. and stirred for 2 hours. The reaction mixture was cooled to 20° C. to 25° C. and pH was adjusted to 7.5 to 8.0 with 5% NaOH. The solution was filtered and washed with mixture of acetonitrile and water and dried at 50° C. to 55° C. to obtain [R—(R*,R*)]-1,1-dimethylethyl-2-(4-fluorophenyl)-dihydroxy-5-(1-methylethyl)-3-phenyl-4-[(phenylamino) carbonyl]-1H-pyrrole-1-heptanoate.

Example-2

Preparation of Amorphous Atorvastatin Calcium

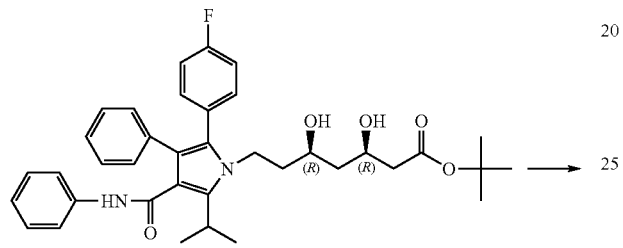

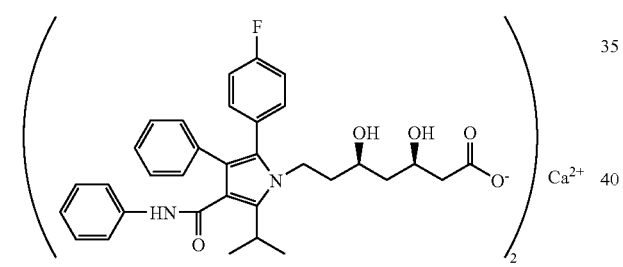

20 gm of R—(R*,R*)]-1,1-dimethylethyl-2-(4-fluorophenyl)-dihydroxy-5-(1-methylethyl)-3-phenyl-4-[(phenylamino) carbonyl]-1H-pyrrole-1-heptanoate was taken in 400 mL of acetonitrile to obtain clear solution at 40° C. to 45° C. The reaction mixture was cooled to 25° C. to 30° C. and 2.60 gm of NaOH solution in 100 mL of water was added within 15 min and stirred for 30 min. Acetonitrile was distilled under vacuum to obtain white slurry or solid. The compound thus obtained was further cooled at 10° C. to 15° C. 400 mL of water was added followed by slow addition of 400 mL of ethyl acetate to dissolve the solution. 10.46 gm of calcium acetate solution in 244 mL of water was added to obtain hazzy solution at 10° C. to 15° C. The reaction mixture was stirred for 2 hrs at 35° C. to 40° C. and cooled to 30° C. to 35° C. The organic layer was separated and washed with water and filtered through hyflow bed followed by washing with ethyl acetate. The organic phase was distilled to remove ethyl acetate completely till powder or lump of material was obtained. The solid thus obtained was treated with 100 mL of cyclohexane and stirred for 30 min. The product was filtered, washed with cyclohexane and dried at 30° C. to 35° C. to obtain amorphous atorvastatin calcium.

Example-3

Preparation of Amorphous Atorvastatin Calcium

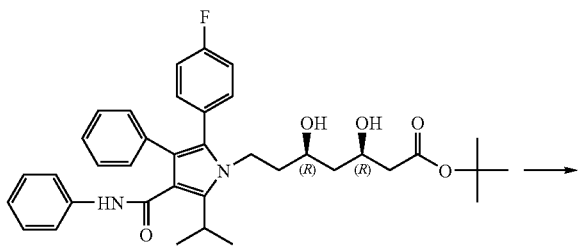

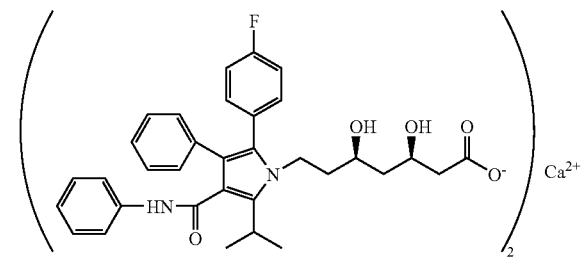

20 gm of R—(R*,R*)]-1,1-dimethylethyl-2-(4-fluorophenyl)-dihydroxy-5-(1-methylethyl)-3-phenyl-4-[(phenylamino) carbonyl]-1H-pyrrole-1-heptanoate was taken in 400 mL of acetonitrile to obtain clear solution at 40° C. to 45° C. The reaction mixture was cooled to 25° C. to 30° C. and 2.60 gm of NaOH solution in 100 mL of water was added within 15 min and stirred for 30 min. Acetonitrile was distilled under vacuum to obtain white slurry or solid. The compound thus obtained was further cooled at 10° C. to 15° C. 400 mL of water (with pH≈8.0 adjusted by liquor ammonia) was added followed by slow addition of 400 mL of ethyl acetate to dissolve the solution. 3.48 gm of calcium acetate solution in 80 mL of water was added to obtain hazzy solution at 10° C. to 15° C. followed by addition of liquor ammonia to adjust the pH≈8.0. The reaction mixture was stirred for 2 hrs at 35° C. to 40° C. and cooled to 30° C. to 35° C. The organic layer was separated and washed with water and filtered through hyflow bed followed by washing with ethyl acetate. The organic phase was distilled to remove ethyl acetate completely till powder or lump of material was obtained. The solid thus obtained was treated with 100 mL of cyclohexane and stirred for 30 min. The product was filtered, washed with cyclohexane and dried at 30° C. to 35° C. to obtain amorphous atorvastatin calcium.

Example-4

Preparation of Amorphous Atorvastatin Calcium

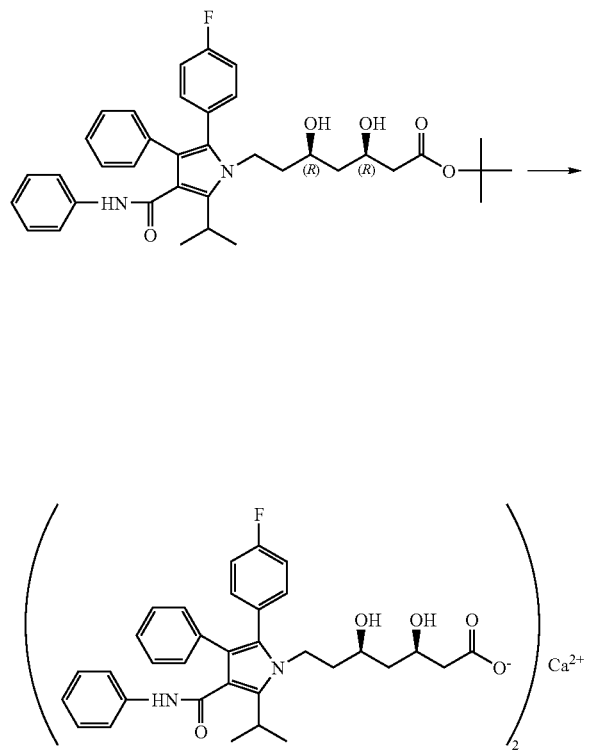

20 gm of R—(R*,R*)]-1,1-dimethylethyl-2-(4-fluorophenyl)-dihydroxy-5-(1-methylethyl)-3-phenyl-4-[(phenylamino)carbonyl]-1H-pyrrole-1-heptanoate was taken in 400 mL of acetonitrile to obtain clear solution at 40° C. to 45° C. The reaction mixture was cooled to 25° C. to 30° C. and 2.60 gm of NaOH solution in 100 mL of water was added within 15 min and stirred for 30 min. Acetonitrile was distilled under vacuum to obtain white slurry or solid. The compound thus obtained was further cooled at 10° C. to 15° C. 400 mL of water was added followed by slow addition of 400 mL of ethyl acetate to dissolve the solution. 10.46 gm of calcium acetate solution in 244 mL of water was added to obtain hazzy solution at 10° C. to 15° C. The reaction mixture was stirred for 2 hrs at 35° C. to 40° C. and cooled to 30° C. to 35° C. The organic layer was separated and washed with water and filtered through hyflow bed followed by washing with ethyl acetate. The organic layer was treated with butylated hydroxy toluene. The organic phase was then distilled to remove ethyl acetate completely till powder or lump of material was obtained. The solid thus obtained was treated with 100 mL of cyclohexane and stirred for 30 min. The product was filtered, washed with cyclohexane and dried at 30° C. to 35° C. The partially dried wet cake was treated with diethyl ether to obtain slurry. The slurry was filtered and dried to get stabilized atorvastatin amorphous.

Example-5

Preparation of Stable Amorphous Atorvastatin Calcium by (L-lysine/L-Argenine+Water Content 6-8%)

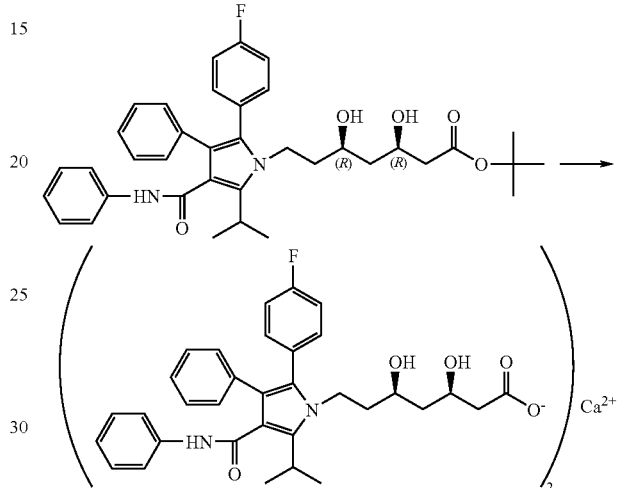

20 gm of R—(R*,R*)]-1,1-dimethylethyl-2-(4-fluorophenyl)-dihydroxy-5-(1-methylethyl)-3-phenyl-4-[(phenylamino)carbonyl]-1H-pyrrole-1-heptanoate was taken in 400 mL of acetonitrile to obtain clear solution at 40° C. to 45° C. The reaction mixture was cooled to 25° C. to 30° C. and 2.60 gm of NaOH solution in 100 mL of water was added within 15 min and stirred for 30 min. Acetonitrile was distilled under vacuum to obtain white slurry or solid. The compound thus obtained was further cooled at 10° C. to 15° C. 400 mL of water was added followed by slow addition of 400 mL of ethyl acetate to dissolve the solution. 10.46 gm of calcium acetate solution in 244 mL of water was added to obtain hazzy solution at 10° C. to 15° C. The reaction mixture was stirred for 2 hrs at 35° C. to 40° C. and cooled to 30° C. to 35° C. The organic layer was separated and washed with water and filtered through hyflow bed followed by washing with ethyl acetate. Ethyl acetate was taken in another RBF and was treated with 30 mg of L-lysine or L-argenine. The organic layer was further treated with butylated hydroxy toluene. The organic phase was then distilled to remove ethyl acetate completely till powder or lump of material was obtained. The solid thus obtained was treated with 100 mL of cyclohexane and stirred for 30 min. The product was filtered, washed with cyclohexane and dried at 30° C. to 35° C. The partially dried wet cake was treated with diethyl ether to obtain slurry. The slurry was filtered and dried to get atorvastatin amorphous. The product thus obtained was humidified under nitrogen atmosphere to obtain stable atorvastatin amorphous calcium with 5-6% water w/w.

Example 6

Preparation of [R—(R*,R*)]-1,1-dimethylethyl-2-(4-fluorophenyl)-dihydroxy-5-(1-methylethyl)-3-phenyl-4-[(phenylamino)carbonyl]-1H-pyrrole-1-heptanoate 100 gm of (3R,5R) tert-butyl (6-{2-[3-phenyl-4-phenylcarbamoyl-2-(4-fluorophenyl)-5-isopropyl-pyrrol-1-yl]-ethyl}-2,2-dimethyl-[1,3]dioxane-4-yl)acetate and 1 Lit acetonitrile were taken in round bottom flask under nitrogen atmosphere. 100 mL 1N HCl solution in 300 mL of water was added dropwise at 25° C. to 35° C. and stirred for 4 to 6 hours. 14.0 g (10%) sodium hydroxide solution was added to the reaction mixture at 25° C. to 35° C. The reaction mixture was treated with 1N HCl to adjust the pH 8.0 to 8.5. Reaction mixture was washed with 1 Lit of diisopropyl ether. Aqueous layer was concentrated under vacuum below 35° C. to distill excess of acetonitrile to obtain thick solid. The solid obtained was treated with 2 L of water, 100 mL of liq. ammonia and 2.5 L of ethyl acetate at 25° C. to 35° C. The reaction mixture was warmed to 40° C. followed by addition of 36.30 g of calcium acetate solution in 400 mL of water. The reaction mixture was stirred for 1 hour and allowed to settle. Separated organic layer was treated 2 times with 1.0 L of 2.5% liq. ammonia and stirred for 15 mins. The separated organic layer was dried over anhydrous magnesium sulfate. After stirring for 30 mins, the reaction mixture was filtered through celite bed and washed with 100 ml ethyl acetate. The ethyl acetate layer was distilled under vacuum at 15° C. to 35° C. till 400 mL of ethyl acetate remain in the solution. The remaining 400 mL of ethyl acetate was filtered through celite bed and washed with 100 ml of ethyl acetate. The ethyl acetate layer was added to precooled 5 Lit of cyclohexane at 10° C. to 20° C. under nitrogen atmosphere. The reaction mixture was stirred for 30 mins and filtered. The wet-cake was washed with 200 mL of cyclohexane and suck dried for 30 mins to obtain amorphous atorvastatin calcium.

500 mL of diethyl ether was taken in round bottom flask under nitrogen atmosphere at 20° C. to 30° C. 100 g of atorvastatin calcium in amorphous form was added into round bottom flask at 20° C. After stirring for 2 hours, amorphous form filtered and washed with 100 mL of diethyl ether. The wet-cake was dried to obtain 92 g (92% of theory) of atorvastatin calcium in amorphous form. The final product is physically stabilized by adding mixture of 0.09 g of butylated hydroxy anisole and 0.135 g of butylated hydroxy toluene and total mixture was subjected to grinding. The product obtained was packed in black polyethylene bag followed by triple laminated aluminum bag with under nitrogen atmosphere at 0° C. to 5° C. to obtain stable amorphous atorvastatin calcium.

FIG. 1 is a graph illustrating the purity of the Atorvastatin calcium derived by the inventive process, in which the intensity in CPS is graphed against the two-theta in degrees.

Example-7

Stability of Atorvastatin Calcium Amorphous

| Related Substance by HPLC | Initial | Cold (5° C.) 2° to 8° C. | 25° ± 2° C./ RH 60 ± 5% | Cold (5° C.) 2° to 8° C. | 25° ± 2° C./ RH 60 ± 5% |
|---|---|---|---|---|---|
| | | 1 Month | | 2 Months | |
| Atorvastatin Diasteroisomer | 0.07% | 0.08% | 0.08% | 0.09% | 0.10% |
| Atorvastatin Desflouro Calcium | 0.06% | 0.06% | 0.05% | 0.07% | 0.06% |
| Atorvastatin Lactone | 0.09% | 0.08% | 0.07% | 0.04% | 0.05% |
| Atorvastatin diol methyl ester | ND | ND | ND | ND | ND |
| 3-O-Methyl Atorvastatin Calcium | 0.02% | 0.03% | 0.02% | 0.03% | 0.03 |
| t-butyl diol ester | ND | ND | ND | ND | ND |
| Atorvastatin protected diol | 0.01% | ND | ND | ND | ND |
| | | 3 months | | 6 Months | |
| Atorvastatin Diasteroisomer | 0.07% | 0.10% | 0.12% | 0.08% | 0.11% |
| Atorvastatin Desfiouro Calcium | 0.06% | 0.07% | 0.06% | 0.05% | 0.06% |
| Atorvastatin Lactone | 0.09% | 0.05% | 0.04% | 0.06% | 0.05% |
| Atorvastatin diol methyl ester | ND | ND | ND | ND | ND |
| 3-O-Methyl Atorvastatin Calcium | 0.02% | 0.03% | 0.03% | 0.03% | 0.03% |
| t-butyl diol ester | ND | ND | ND | ND | ND |
| Atorvastatin protected diol | 0.01% | ND | ND | ND | ND |

What is claimed is:

1. A process for preparation of an amorphous form of atorvastatin calcium of formula I

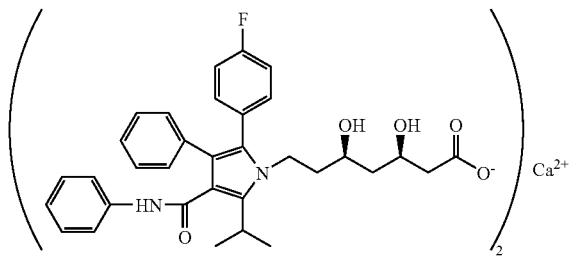

comprising:
   alkaline hydrolysis of a tert-butyl ester of formula (IIa) in a suitable organic solvent;

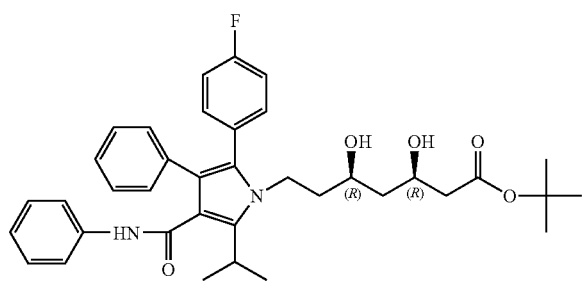

concentrating the reaction mixture to obtain residue;
adding water, ethyl acetate and ammonia to residue;
addition of molar excess of calcium acetate;
separating ethyl acetate layer,
optionally washing ethyl acetate layer with ammonical water;
distilling ethyl acetate and treating with $C_5$-$C_{12}$ hydrocarbon solvent; and optionally slurring amorphous atorvastatin calcium with $C_1$-$C_5$ dialkyl ethers to obtain amorphous atorvastatin calcium.

2. A process according to claim 1, wherein said suitable $C_5$-$C_{12}$ hydrocarbon is selected from pentane, hexane, heptane or cyclohexane.

3. A process according to claim 1, wherein said calcium acetate is used in an amount of from about 1.1 to about 2.5 molar equivalent, preferably about 1.2 to about 1.8, more preferably about 1.5 molar equivalent.

4. A process according to claim 1, wherein said amorphous atorvastatin calcium obtained is optionally treated with dialkylethers $R_1OR_2$ wherein each of $R_1$ and $R_2$ is a $C_1$-$C_5$ alkyl group, preferably with diethylether, diisopropylether or t-butyl-methylether.

5. A process according to claim 1, wherein said suitable organic solvent for alkaline hydrolysis is acetonitrile.

6. A process according to claim 1, wherein the ethyl acetate layer obtained after the extraction is treated with suitable antioxidants.

7. A process according to claim 6, wherein said suitable antioxidants is selected from the group consisting of butylated hydroxyanisole, butylated hydroxytoluene, tertiary-butylated hydroxyquinone, 4-methoxy anisole, preferably butylated hydroxytoluene.

8. A process according to claim 1, wherein said ethyl acetate layer obtained after extraction is treated with ammonia or amino acid selected from L-lysine or L-argenine.

9. A process according to claim 1, wherein amorphous form of atorvastatin calcium obtained is substantially pure amorphous form having single individual unknown impurities less than of about 0.1% and single individual known impurities less than 0.15%.

* * * * *